(12) United States Patent
Yoo et al.

(10) Patent No.: US 11,147,704 B2
(45) Date of Patent: Oct. 19, 2021

(54) CERVICOTHORACIC SPINE RESTORATOR

(71) Applicants: Won Seok Yoo, Oakland, CA (US);
Mahn June Hahn, Daejeon (KR)

(72) Inventors: Won Seok Yoo, Oakland, CA (US);
Mahn June Hahn, Daejeon (KR)

(*) Notice: Subject to any disclaimer, the term of this patent is extended or adjusted under 35 U.S.C. 154(b) by 332 days.

(21) Appl. No.: 16/286,614

(22) Filed: Feb. 27, 2019

(65) Prior Publication Data

US 2019/0262162 A1 Aug. 29, 2019

(30) Foreign Application Priority Data

Feb. 28, 2018 (KR) .................. 10-2018-0024381

(51) Int. Cl.
*A61F 5/02* (2006.01)
*A61H 1/00* (2006.01)
*A61H 1/02* (2006.01)

(52) U.S. Cl.
CPC .............. *A61F 5/028* (2013.01); *A61F 5/024* (2013.01); *A61F 5/026* (2013.01); *A61H 1/008* (2013.01); *A61H 1/0296* (2013.01); *A61H 1/0218* (2013.01)

(58) Field of Classification Search
CPC ........ A61F 5/01; A61F 5/055; A61F 5/05883; A61F 5/3707; A61F 13/12; A61F 13/128; A61F 5/012; A61F 5/05816; A61F 5/028; A61F 5/026; A61F 5/024; A42B 3/0473
See application file for complete search history.

(56) References Cited

U.S. PATENT DOCUMENTS

| | | | | |
|---|---|---|---|---|
| 5,279,310 A | * | 1/1994 | Hsien | A61F 5/01 128/DIG. 20 |
| 5,382,226 A | * | 1/1995 | Graham | A61H 1/0218 128/845 |
| 7,670,307 B2 | * | 3/2010 | Chitwood | A61H 1/0296 602/13 |
| 2013/0112213 A1 | * | 5/2013 | Bhat | A47C 27/081 128/889 |
| 2013/0204169 A1 | * | 8/2013 | Poepperling | A61H 23/02 601/46 |
| 2017/0112702 A1 | * | 4/2017 | Kim | A47C 7/46 |

FOREIGN PATENT DOCUMENTS

| | | |
|---|---|---|
| CN | 204889439 U | 12/2015 |
| KR | 10-1445261 B1 | 9/2014 |
| KR | 10-1564502 B1 | 10/2015 |
| KR | 10-2016-0076068 A | 6/2016 |

* cited by examiner

*Primary Examiner* — Ophelia A Hawthorne
(74) *Attorney, Agent, or Firm* — Park, Kim & Suh, LLC

(57) ABSTRACT

A cervicothoracic spine restorator is disclosed. In the cervicothoracic spine restorator, a fixing structure is further included, such that relaxation of muscles such as pectoralis major muscle, pectoralis minor muscle, rectus abdominis muscle, and trapezius muscle or latissimus dorsi muscle can be easily performed. Further, the blood vessel may be expanded and the blood may be supplied smoothly to the head. This may help recovery and correction during a short correction period. There is an advantage that a separate correction mechanism, which is used for spine correction such as a abdomen band, is unnecessary.

16 Claims, 14 Drawing Sheets

100

122

CERVICOTHORACIC SPINE RESTORATOR

CROSS-REFERENCE TO RELATED APPLICATION

This application claims a benefit under 35 U.S.C. § 119(a) of Korean Patent Application No. 10-2018-0024381 filed on Feb. 28, 2018, on the Korean Intellectual Property Office, the entire disclosure of which is incorporated herein by reference for all purposes.

BACKGROUND

1. Field

The present disclosure relates to a correction apparatus, in particular to a spine or cervical/thoracic spine correction apparatus.

2. Description of Related Art

Generally, a spine of a human body is subjected to energy shortage and tissue tension (contraction) of spine surrounding tissues including spinal erector muscles due to factors such as aging and stress or incorrect long-term postural state. This may lead to a pathological curvature of the spine (kyphosis and scoliosis) or to an abnormal pressure on the spine bone itself.

Such long-term contraction of the spine surrounding tissues reduces blood circulation, thereby increasing anaerobic metabolism due to decreased oxygen supply into tissues, thereby causing energy (ATP) production decrease and accumulation of lactic acid. This results in chronic myalgia around the spine and a local temperature drop, thereby creating a vicious loop in which the spine surrounding tissue contracts further.

This contraction of the spine surrounding tissue narrows a spacing between adjacent bones of the spine, thereby loosening a ligament and a joint capsule surrounding a joint. This may result in drifting structures such as facet joints of the spine from their normal anatomical locations, thereby causing subluxation as deviation from the normal location and thus resulting in a pain and activity limitation.

Further, the excessive pressure onto the spine in the long term induces degeneration of the disc by over-pressing the disc. This causes compression of spinal nerves, resulting in causing symptoms of the spinal stenosis or disc symptoms due to escape of the disc nucleus pulposus.

Thus, the abnormal pressure applied to the spine for a long period of time causes calcium deposits in the margin of the spine bone to form osteophyte. This causes friction with the surrounding tissues and compress nerves adjacent to the spine and eventually transforms the spine bone itself into a wedge shape. Thus, this may lead to the spine kyphosis state, in which the back bone is permanently curved, or the pathologic spine scoliosis together with rotational deformation of the spine.

Further, this long-term kyphosis condition shrinks the entire body's soft tissue.

Therefore, in order to solve the problem of the abnormal spine arrangement as described above and recover the normal elected state, correcting the spine itself, and reducing the contraction of the soft tissue around the spine may be required. In particular, relaxation of the soft tissues throughout the body must be considered.

Conventionally, in order to improve the alignment state of the spine, ancient Chinese artificial spine correction, chiropractic, ancient Indian spine correction instrument Kurunta, a thermal heating bed capable of the spine compression via a movement of a press-contacting rod, and a deformable chair with a 180-degree rotation have been employed.

In this regard, in one prior art, Korean Patent No. 10-1445261 (hereinafter referred to as "Prior Art 1") provides a backrest-type chiropractic treatment device of triply curved structure including a spin-supporting plate having an arched upper part where a back and waist touch to distribute a load applied on a spine of a human body, an inverted arched lower part where hips touch, and a sliding groove at the center part to allow a pressing roller to vertically slide along the spine; and a spine acupressure-treatment means on the rear surface of the spin-supporting plate to enable the pressing roller to perform acupressure treatment on the spine of a human body while sliding along the sliding groove. The backrest-type chiropractic treatment device of a triply curved structure presses or relaxes the front side of a human body and a physiologically curved body part while the pressing roller slides, thereby correcting abnormally curved spin.

In the prior art 1, the backrest-type chiropractic treatment device of a triply curved structure may allow relieving the pathologic curvature of a spine (kyphosis) and improving the circulation of soft tissues around the spine and neural transmission.

However, in the prior art 1, there is a disadvantage in that a secondary accident may be caused by the movement of the user body because means for fixing the users body is not separately provided therein.

In this regard, in another prior art, Korean Patent No. 10-1564502 (hereinafter referred to as "Prior Art 2") provides a device for correcting the backbone. The device includes a bottom plate; an elastic curve that is installed to be extended upwards in a curved shape from one end of the bottom plate, has one end of the body thereof separated at a particular distance from the top surface of the bottom plate, and supports the user waist and back when he/she lies back thereon, so that his/her backbone is corrected; a first projection part formed to protrude along one side top surface of the elastic curve; a second projection part formed to protrude along one side top surface of the elastic curve to be separated at a particular distance from the first projection part; a backbone correcting groove formed on the top surface of the elastic curve between the first projection part and second projection part so that the backbone of the user is disposed thereon when the user lies back thereon and so that the backbone of the user is corrected; and a height adjusting means installed to be separated at a particular distance from between the top surface of the bottom plate and one end bottom surface of the elastic curve so as to adjust the height of the elastic curve.

In the prior art 2, the device has a simple configuration so as to be easily stored and moved. The device also has a height adjusting means so that a user can easily correct his/her backbone at a height that he/she wants. However, the device may not support the cervical spine due to a fact that the device is configured so that only the user's waist spine may be corrected.

In this regard, in still another prior art, Korean Patent Application Publication number 10-2016-0076068 (hereinafter referred to as "Prior Art 3") provides a corrective back pillow. The corrective back pillow has elasticity, supports from a head to thigh of human body, and includes a head supporting part, a cervical-spine supporting part, a scapula supporting part, a chest supporting part, a waist supporting part, a buttock supporting part, and a thigh supporting part which are formed according to shapes of regions of the human body.

In the prior art 3, the corrective back pillow provides a customized corrective back pillow which is capable of preventing or correcting straight neck or military neck by forming a cervical-spine supporting portion and a shape corresponding to ideal head movement lines of a user during remedying of bony framework in a semicircular protruded shape on the basis of the center of back of the head.

However, in the prior art 3, there is a disadvantage in that since the pillow is not fixed, the correction is not sufficiently performed due to the separation of the pillow during the sleeping.

In this regard, in still another prior art, Chinese Utility Model Publication No. 204889439 (hereinafter referred to as 'Prior Art 4') discloses a lumbar spine portion-integrated pillow which is formed so that a user's waist muscle can be easily relaxed.

When the pillow of the prior art document 4 is used, there is an advantage that a structure supporting a lower body is further included to support the feet of the user. However, since the pillow is detached from the user body due to the user's turning over during sleep, the correction is not sufficient.

SUMMARY

The present disclosure aims at solving the problems of the prior arts, and has a purpose of providing a cervicothoracic spine restorator of being able to correct not only the spine of the user but also the cervical spine, thereby preventing and correcting the straight neck or military neck.

In addition, the present disclosure has a purpose of providing a cervicothoracic spine restorator in which a fixing structure is further included, such that relaxation of muscles such as pectoralis major muscle, pectoralis minor muscle, rectus abdominis muscle, and trapezius muscle or latissimus dorsi muscle can be easily performed, which is advantageous for muscle stretching.

In one aspect of the present disclosure, there is provided a cervicothoracic spine restorator comprising: a main body having a curved outer top face closely contacting a cervical spine and a spine in a fixed manner; and fixing means including a fixing strap outwardly extending from a right or left side face of the main body and protruding outwardly to surround a lower side face of the main body.

In one implementation, the main body includes: a cervical spine support portion protruding upwardly to support a cervical spine to be kept in a C-shape, wherein a head support groove is defined in the cervical spine support portion; and a back support portion extending downwardly from the cervical spine support portion and protruding outwardly, wherein the back support portion includes a spine support portion to support a spine to be kept in a C-shape and to be fixed in a correct position.

In one implementation, the back support portion includes a recess inwardly defined in a right or left lateral edge thereof to facilitate contraction of a back muscle.

In one implementation, the restorator (correction apparatus) further comprises head fixing means spaced from a top of the cervical spine support portion to surround a head and fix the head; and forehead fixing means protruding outwardly from one side of the head fixing means to fix a forehead.

In one implementation, the apparatus further comprises at least one roughness structure protruding outwardly from a top of the main body.

In one implementation, the apparatus further comprises a rotating protrusion protruding outwardly from a top face of the main body, wherein the rotating protrusion is configured to vibrate or rotate based on an electrical signal from a controller disposed inside the main body.

In one implementation, the apparatus further comprises a pharmaceutical pad disposed on a top face of the main body so as to protrude outwardly therefrom, wherein the pharmaceutical pad contains a topical analgesic.

The apparatus further comprises: a housing protruding outwardly to surround an edge of the pharmaceutical pad; a housing cover formed inside the housing so as to cover an outer face of the housing; a housing fixing portion protruding outwardly from one face of the housing cover; and a housing locking portion protruding in a direction facing the housing cover from a face of the housing, wherein the housing fixing portion is engaged with the housing locking portion to fix the housing cover.

In one implementation, the apparatus further comprises: a height adjustment unit contained in the main body; a height maintaining portion extending horizontally from a top of the height adjustment unit; a height adjustment unit support disposed below the height adjustment unit, wherein the height adjustment unit support is configured to adjust a vertical position of the height adjustment unit; and a slid portion configured to allow the height adjustment unit support to slidably move on a bottom face of the main body along the slid portion.

In one implementation, the apparatus further comprises an expandable or shrinkable portion disposed on the main body to expand or shrink the main body or to divide the main body into two portions.

In accordance with the present disclosure, the apparatus may be used to correct not only the user's spine but also the cervical spine thereof, thereby preventing and correcting the straight or military neck, shoulder or arm pain, shoulder stiffness, etc. Furthermore, the main body is formed to support the spine and the cervical spine. The C-shaped portion support the cervical spine. Thus, easy breathing helps prevent or alleviate snoring.

In addition, the fixing structure is further included, such that relaxation of muscles such as pectoralis major muscle, pectoralis minor muscle, rectus abdominis muscle, and trapezius muscle or latissimus dorsi muscle can be easily performed, which is advantageous for muscle stretching. Further, the blood vessel may be expanded and the blood may be supplied smoothly to the head. This may help recovery and correction during a short correction period. There is an advantage that a separate correction mechanism, which is used for spine correction such as a abdomen band, is unnecessary.

Relaxing the thoracic spine according to the shape of the main body may allow a correct posture maintenance of the thoracic spine, back muscles, etc. to be achieved. Further, this may relax the tension caused by contraction of the chest muscles due to an incorrect posture.

Further, the cervical spine decompression or lumbar disc traction therapy are effective.

DETAILED DESCRIPTIONS

Figure 1:
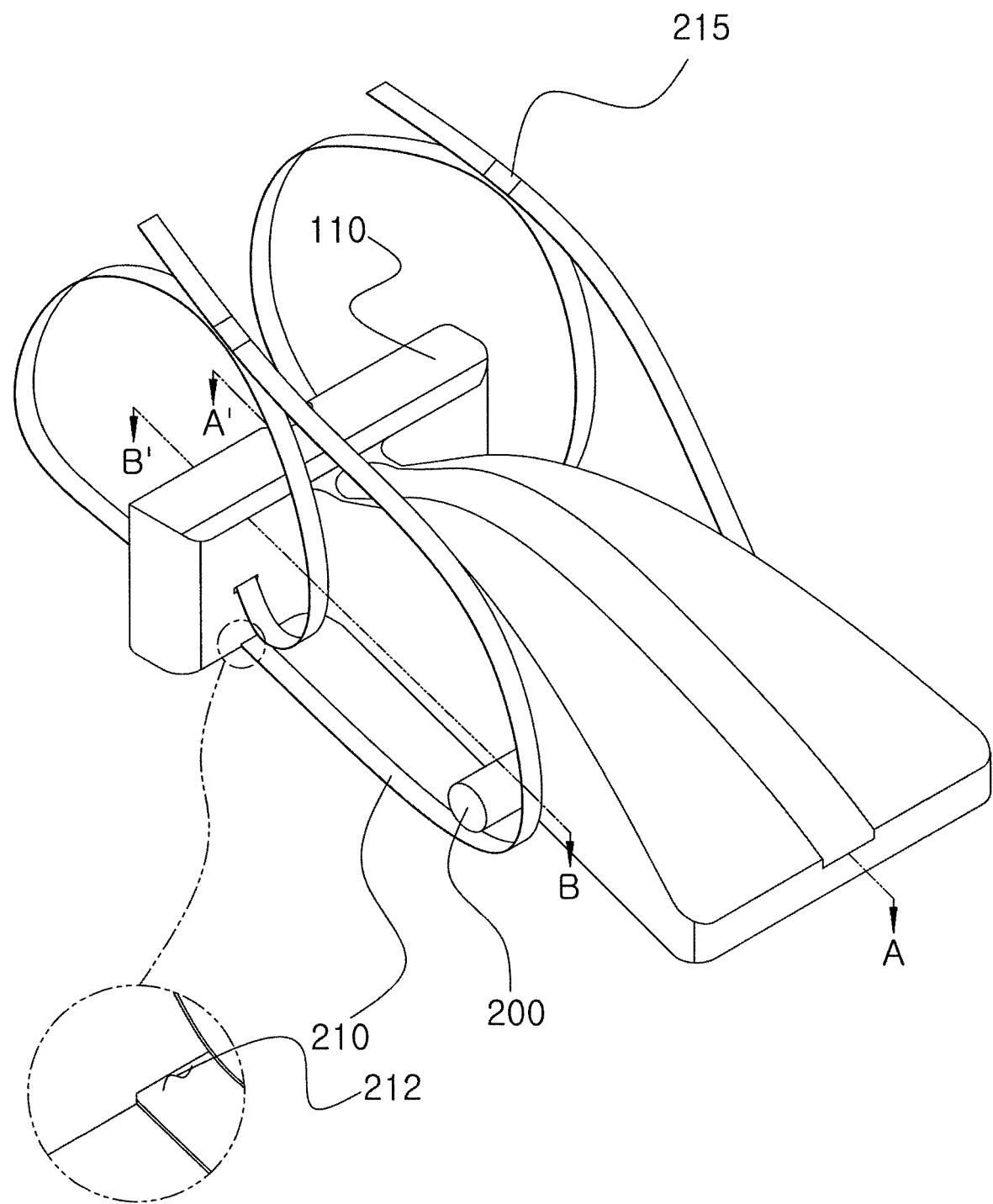
FIG. 1 is a perspective view of a cervicothoracic spine restorator according to the present disclosure.
Figure 2:
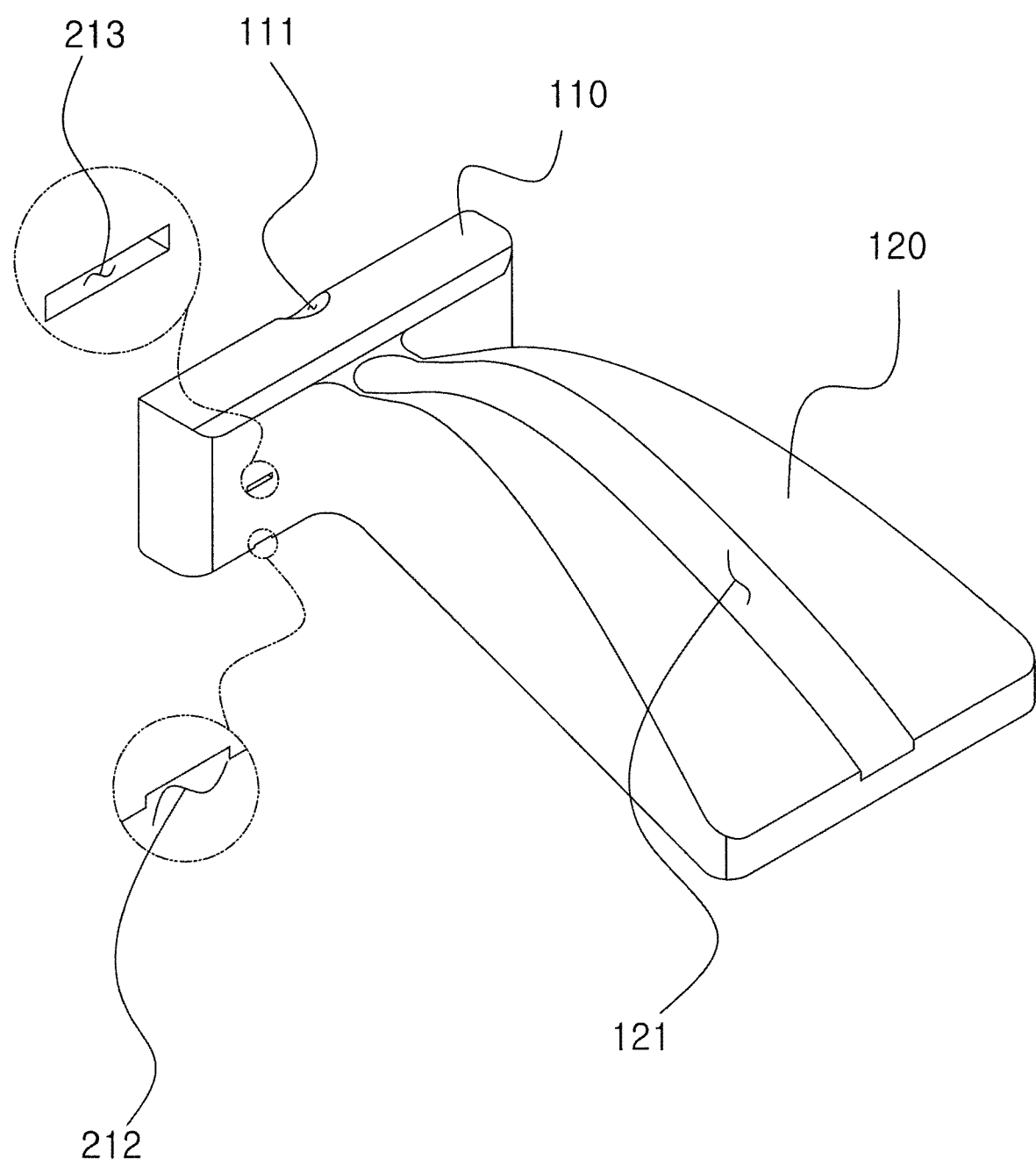
FIG. 2 is a perspective view of a main body according to the present disclosure.

Examples of various embodiments are illustrated and described further below.

For simplicity and clarity of illustration, elements in the figures are not necessarily drawn to scale. The same reference numbers in different figures denote the same or similar elements, and as such perform similar functionality.

Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiment 1

As shown in FIG. 1 to FIG. 4, a cervicothoracic spine restorator according to the present disclosure may include a main body 100 and arm or shoulder fixing means 200.

More specifically, the main body 100 may have a curved outer face such that the cervical spine and the spine may closely contact the curved outer face.

In addition, the main body 100 includes a cervical spine support portion 110 and a back support portion 120. Thus, the main body 100 may be shaped to easily correct the spine as well as the cervical spine.

The cervical spine support portion 110 defines a top portion of the main body 100 and supports the cervical spine. The cervical spine support portion 110 may be formed to protrude upward so that the C-shape is defined between the cervical spine support portion 110 and the back support portion 120. Thus, the cervical spine may conform to the C-shaped portion. The cervical spine support portion 110 includes a head support groove 111 in which the head is received.

Preferably, the C-shaped portion is formed such that a series of third to fifth cervical spine discs of the seven cervical spine discs are curved upwards. Thus, the military neck, shoulder and arm pain, shoulder stiffness or straight neck may be easily corrected or healed.

Accordingly, the fifth through seventh cervical spine discs are relaxed, thereby alleviating the user's neck disc pain.

Furthermore, the main body is formed to support the spine and the cervical spine. The C-shaped portion support the cervical spine. Thus, easy breathing helps prevent or alleviate snoring.

In this connection, the head support groove 111 may be formed such that an edge of the cervical spine support portion 110 is recessed in a gentle curve so that the user's head can be easily fixed thereon.

Thus, the head of the user is stably seated in the head support groove 111 defined in the cervical spine support portion 110. This may prevent a damage caused by a sharp edge. Further, the spine may also be properly seated in the correct position on the back support portion 120 to be described later.

Next, the back support portion 120 extends downward from the cervical spine support portion 110. The back support portion 120 includes a spine support portion 121 that allows the spine to be maintained in a C-shape and allow the spine to be seated in the correct position.

Preferably, the spine support portion 121 is formed such that the thoracic spine is be maintained to be curved upwards. As the shoulder is fixed, the spine may be easily corrected.

More preferably, the spine support portion 121 is formed such that the array of the second through seventh thoracic spine discs of the twelve thoracic spine discs is maintained to be curved in the upward direction. The present disclosure is not limited thereto.

In this connection, the spine support portion 121 may be formed to be recessed inwardly in the top face of the back support portion 120 and extend in the longitudinal direction thereof.

When the spine support portion 121 is formed to be recessed inwardly, and when the spine contacts the top face of the back support portion 120, the spine may be seated on the correct position of the back support portion 120 without using an auxiliary device such as a mirror.

In addition, a width of an upper portion of the back support portion 120 is smaller than a width of a lower portion of the back support portion 120. That is, the back support portion 120 is tapered downwards.

This causes the shoulder of the user to abut the lower side face of the cervical spine support portion 110 when the user's back is seated on the back support portion 120. Thus, the shoulder relaxation may be easily performed.

Figure 3:
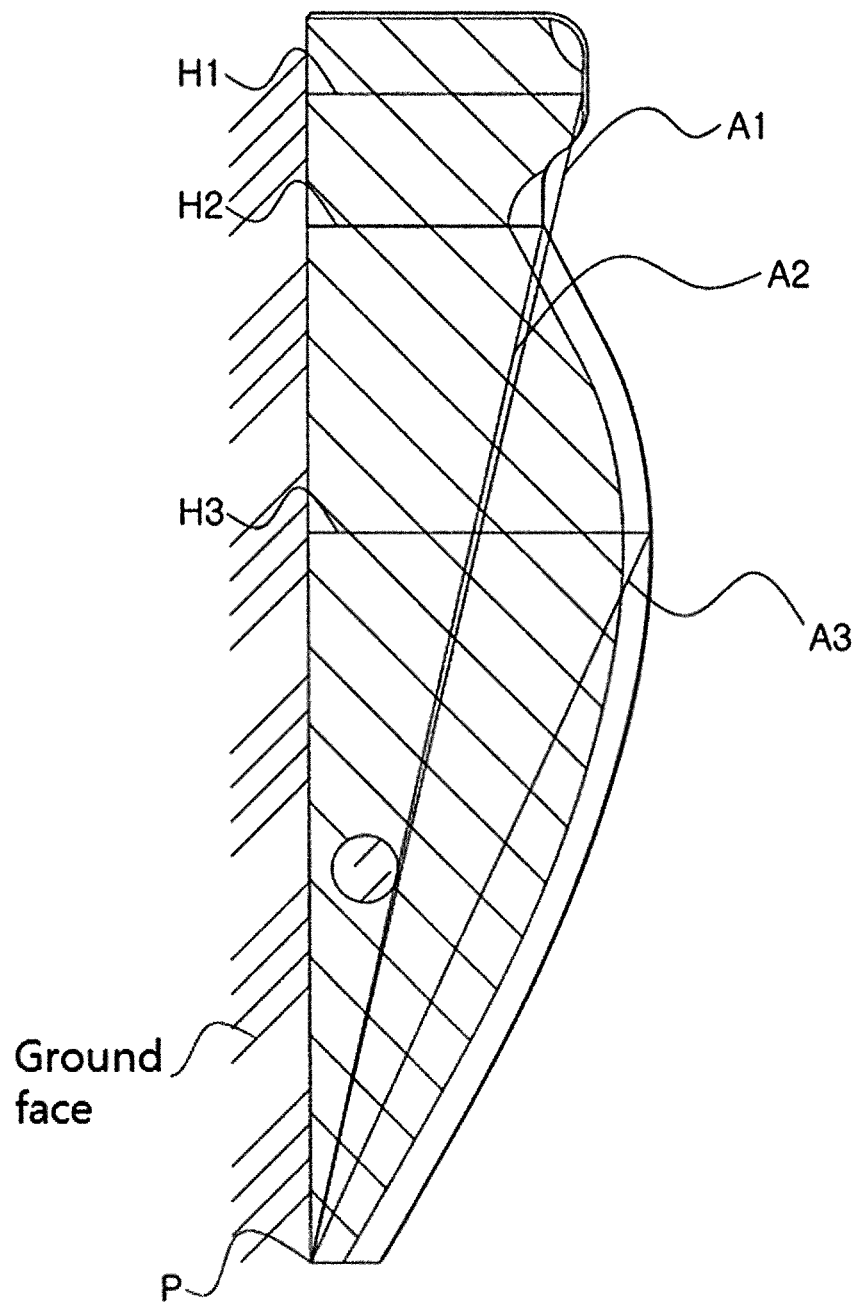
FIG. 3 is a cross-sectional view taken along a line A-A' of the cervicothoracic spine restorator according to the present disclosure.

As shown in FIG. 3, when the main body 100 is fixed on the ground, the maximum vertical dimension of the cervical spine support portion 110 is denoted by H1. A height of the connecting portion between the cervical spine support portion 110 and the back support portion 120 is H2. the maximum vertical dimension of the back support portion 120 is H3. H1:H2:H3 may be in a range of 1:0.75 to 0.95:0.85 to 1.15.

Further, a bottom end point of the cervicothoracic spine restorator is defined as P. A line between the P point and the peak point of the cervical spine support portion 110 is A1. A line between the point P and the peak point of the connection point between the cervical spine support portion 110 and the back support portion 120 is A2. A line between the point P and the peak of the back support portion 120 is A3. In this case, a angle between the line A1 and the ground face: the angle between the line A2 and the ground face: an angle between the line A3 and the ground face may be in the range of 1:0.5 to 1:1 to 2.

When H1:H2 is smaller than 1:0.75, the H2 height causes a gap between the user's shoulder and the cervicothoracic spine restorator. Thus, there is a disadvantage in that the shoulder relaxation of the user is not easily performed. When H1:H2 is larger than 1: 0.95, the thoracic spine is maintained in a linear shape rather than a C-shape. This has the disadvantage that spine correction cannot be performed easily.

Furthermore, when H1:H3 is smaller than 1:0.85, the H2 is small, and, thus, the user's spine cannot be maintained in a curved shape, so that the shoulder cannot easily be relaxed. When H1:H3 is larger than 1:1.15, the cervical spine is not fixed in the correct position, due to the height of the H2, and thus the cervical spine cannot be easily corrected.

Further, when the angle between A1 and the ground face: A2 and the ground face is smaller than 1:0.5, due to the angle between A2 and the ground face, the height of H2 becomes lower. Thus, a gap is formed between a user's shoulder and the cervicothoracic spine restorator, so that a user's shoulder relaxation cannot be performed easily. When the angle between A1 and ground face: an angle between A2 and the ground face is greater than 1:1, due to the angle between A2 and the ground face, H2 becomes larger than H1. This makes it difficult for the user's cervical spine to be maintained in a C-shape.

Further, when the angle between A1 and the ground face: A3 and the ground face is smaller than 1:1, due to the angle between A3 and the ground face, the height of H3 becomes smaller. Thus, this makes it difficult for the user's spine to be maintained in a C-shape. Thus, a user's shoulder relaxation cannot be performed easily. When the angle between A1 and ground face: an angle between A3 and the ground face is greater than 1:2, due to the angle between A3 and the ground face, H3 becomes larger. Thus, a user's shoulder relaxation cannot be performed easily.

Therefore, relaxing the thoracic spine according to the shape of the main body may allow a correct posture maintenance of the thoracic spine, back muscles, etc. to be achieved. Further, this may relax the tension caused by contraction of the chest muscles due to an incorrect posture. Further, the cervical spine decompression or lumbar disc traction therapy and other advantages are effective.

Figure 5:
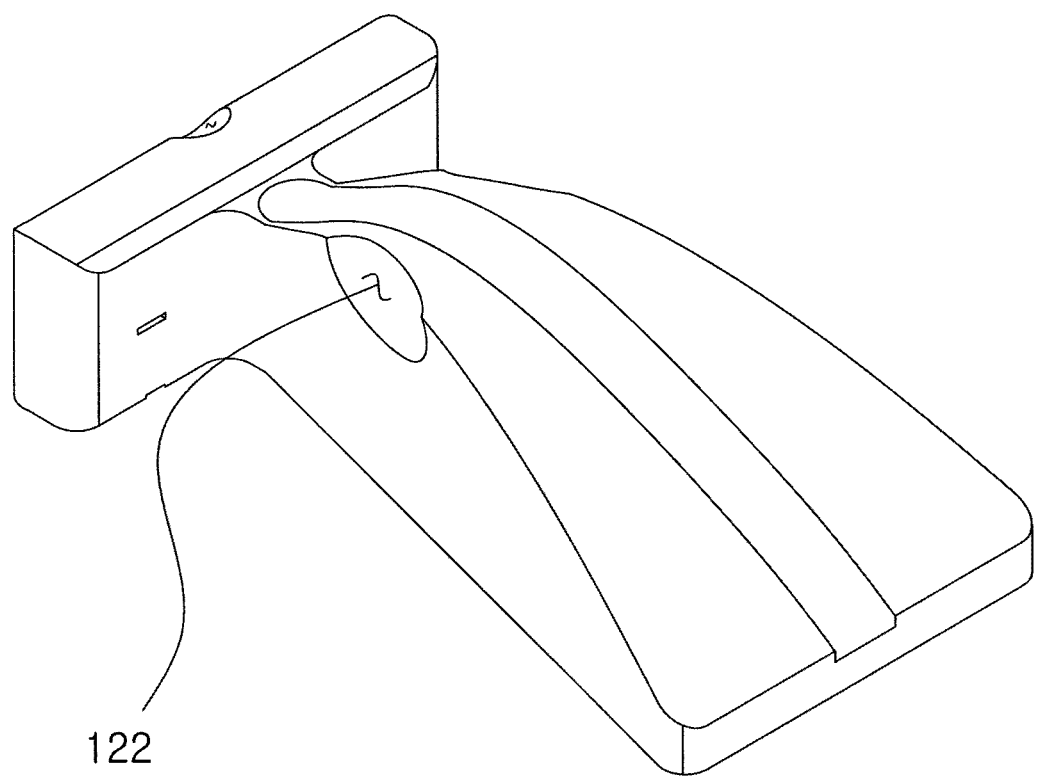
FIG. 5 is a perspective view of a main body according to an embodiment of the present disclosure.

In addition, as shown in FIG. 5, a recess 122 may be optionally formed in any one of the left or right side edge of the back support portion 120 to facilitate contraction of the user's back muscles.

Due to the presence of the recess 122, there is an advantage that when a user's shoulder or arm is fixed by the arm or shoulder fixing means 200 as described later, the back muscles of the user are not pressed against the sharp edge of the back support portion 120 and thus the correct posture may be maintained for a long time.

Next, the arm or shoulder fixing means 200 includes a strap support extending perpendicularly to the longitudinal direction of the main body from the left or right side of the main body 100. The arm or shoulder fixing means 200 includes a fixing strap 210 that attaches to or winds around the strap support and fixes the user's arm or shoulder.

The fixing strip 210, which will be described later attaches to or winds around the strap support and fixes the user's arm or shoulder. Thus, the relaxation of muscles such as pectoralis major muscle, pectoralis minor muscle, rectus abdominis muscle, and trapezius muscle or latissimus dorsi muscle can be easily performed, which is advantageous for muscle stretching.

Further, the fixing strap 210 winds around the strap support of arm or shoulder fixing means 200 and can easily fix the shoulder or arm. The present disclosure is not limited thereto.

Preferably, the shape of the strap support of the arm or shoulder fixing means 200 is formed in a cylindrical shape such that the fixing strap 210 may easily wrap the strap support.

Figure 6:
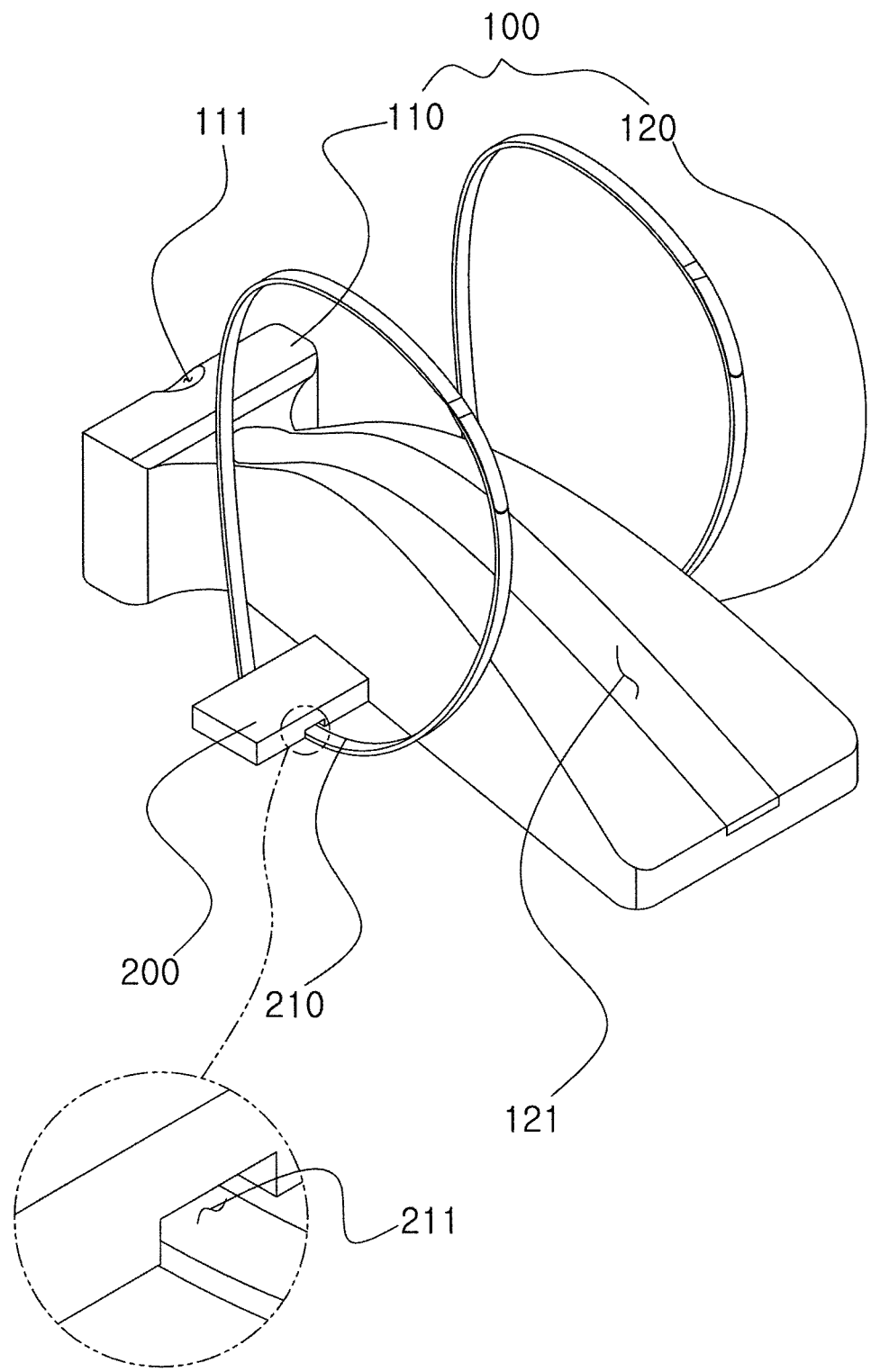
FIG. 6 is a perspective view of a cervicothoracic spine restorator according to an embodiment of the present disclosure.

A strap receiving groove 211 is defined in the bottom face of the strap support of the arm or shoulder fixing means 200, as shown in FIG. 6. Thus, the fixing strap 210 is firmly attached to the strap support without slipping along the strap support of the arm or shoulder fixing means 200.

That is, the fixing strap 210 is inserted into the strap receiving groove 211. As a result, when the user wears the cervicothoracic spine restorator, the user can freely perform arm or shoulder motion. The user may move freely while wearing the cervicothoracic spine restorator. When the user is sitting on a chair, the user may continuously perform a correction of the spine or cervical spine.

Figure 4:
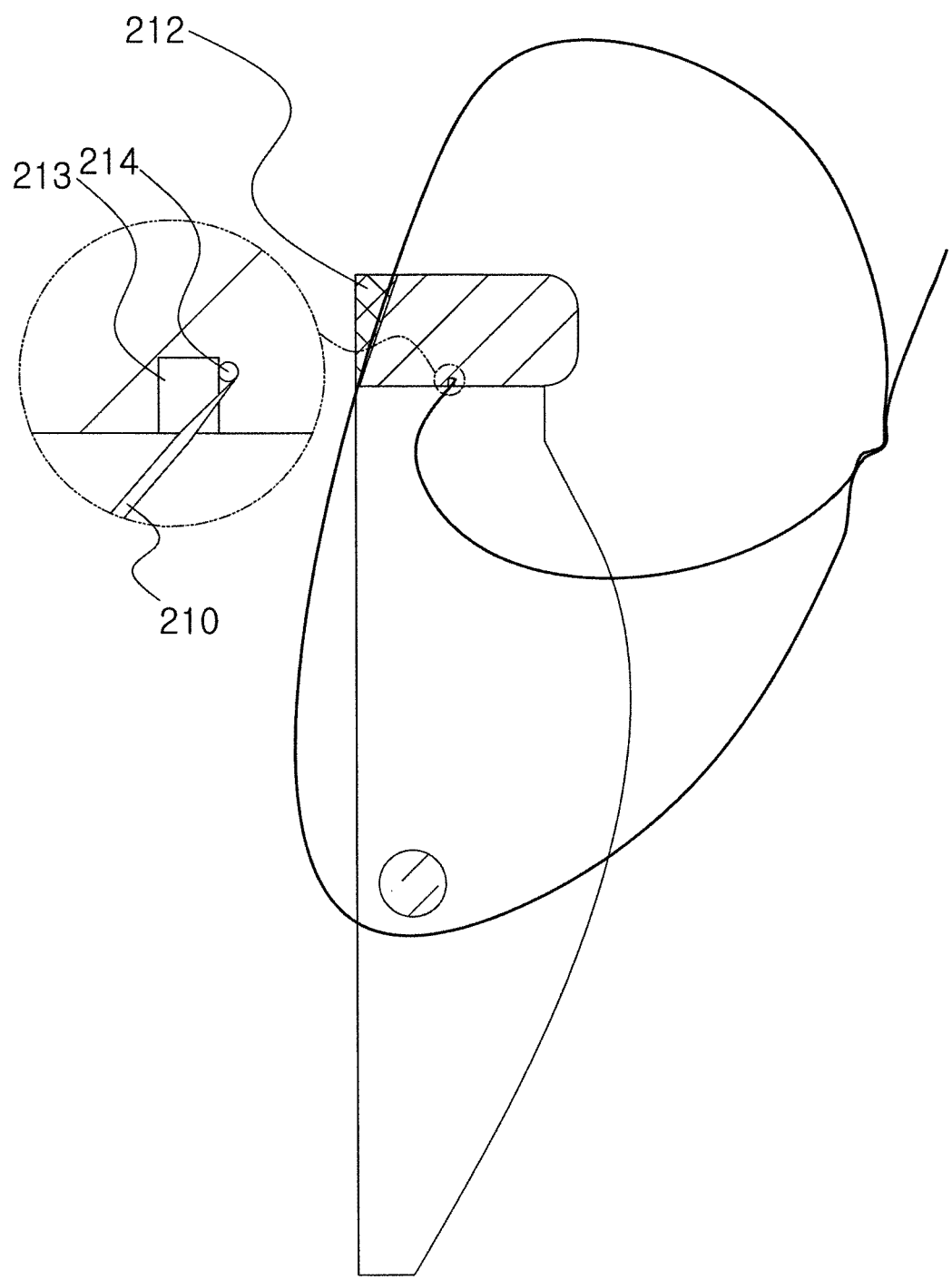
FIG. 4 is a cross-sectional view taken along a line B-B' of the cervicothoracic spine restorator according to the present disclosure.

As shown in FIGS. 1 and 4, the fixing strap 210 extends from and surrounds the cervical spine support portion 110 to easily secure the user's shoulder or arm. A further strap receiving groove may be defined in the bottom face of the cervical spine support portion 110. Thus, the fixing strap 210 may be fitted into the further strap receiving groove.

Preferably, the fixing strap 210 may extend from a lower side face of the cervical spine support portion 110. The present disclosure is not limited thereto.

In order to easily fix the fixing strap 210 to the cervical spine support portion 110, a fixing strap receiving groove 213 and fixing strap fixing means 214 may be further included.

The fixing strap receiving groove 213 may be formed in a groove shape in a bottom face of the cervical spine support portion 110 so that the fixing strap 210 may easily fix the shoulder or arm of the user.

In this connection, the fixing strap fixing means 214 may be disposed in the fixing strap receiving groove 213 such that the fixing strap 210 may be further secured to the fixing strap receiving groove 213 to further prevent the fixing strap 210 from being separated from the fixing strap receiving groove 213.

Thus, the fixing strap 210 may wrap around the cervical spine support portion 110. Further, the fixing strap 210 may wrap around the strap support of the arm or shoulder fixing means 200. Thus, the shoulder and arm of the user can be easily brought into close contact with the main body 100.

In this connection, a fixing strap fixing guide 212 may be further included such that the fixing strap 210 may easily be guided along the bottom face of the cervical spine support portion 110.

The fixing strap 210 may not be separated from the bottom face of the cervical spine support portion 110 via the fixing strap fixing guide 212. Thereby, there is an advantage that the damage of the cervical spine support portion 110 due to the deviation of the fixing strap 210 can be prevented.

Further, on a portion of the fixing strap 210, strap length adjustment means 215 embodied as any one selected from Velcro, webbing, leather lock or buckle may be disposed. Thus, the length of the strap 210 can be easily adjusted based on the thickness of the user's shoulder or arm or the like, which, thus, can be fixed via a simple operation.

Embodiment 2

Figure 7:
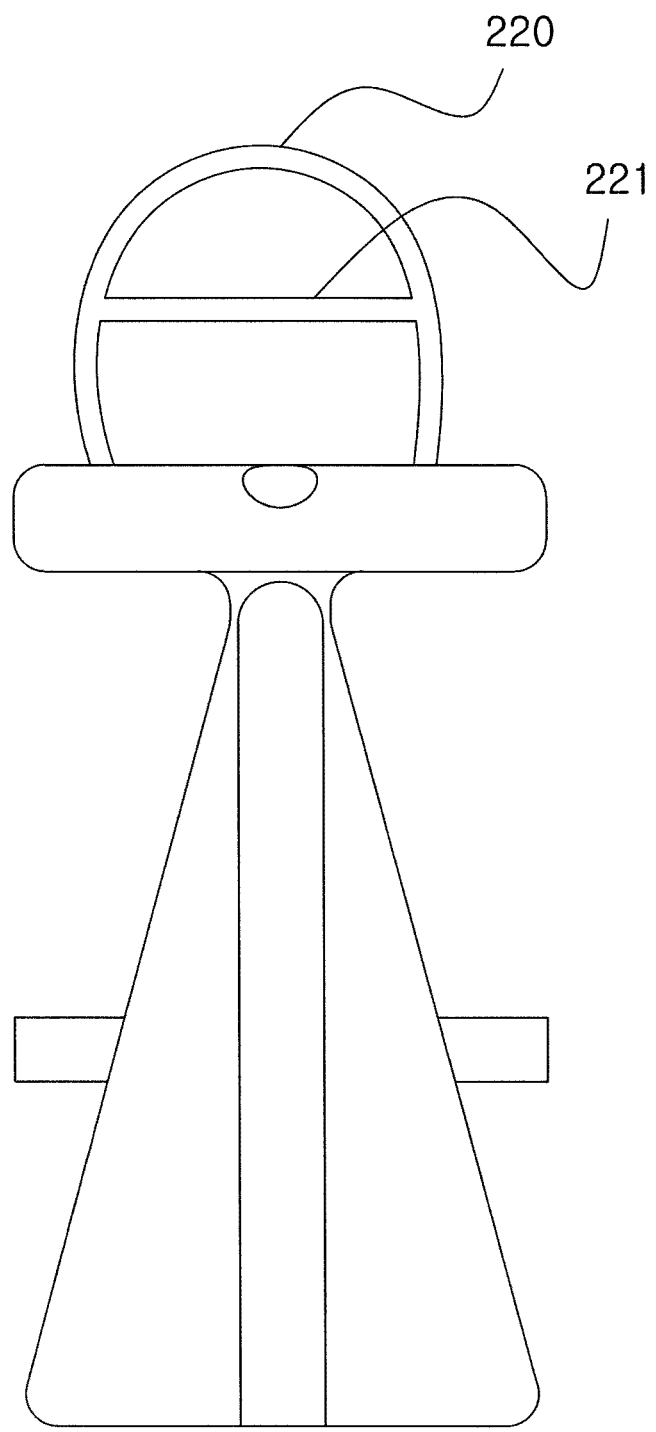
FIG. 7 is a top view of a cervicothoracic spine restorator according to an embodiment of the present disclosure.

Optionally, as shown in FIG. 7, head fixing means 220 and forehead fixing means 221 may further be included.

The head fixing means 220 may extend from an upper side face of the cervical spine support portion 110. The head fixing means 220 may extend from two points of the cervical spine support portion 110 and may form a semi-circular ring.

The head fixing means 220 may fix the head. Thus, when the user uses the cervicothoracic spine restorator during sleep, the correction of the cervical spine and spine may be performed reliably during the sleep by the head fixing means 220 restricting the movement of the head.

In addition, the head fixing means 220 may support the cervical spine, Thus, this achieves the advantage of helping to prevent or alleviate snoring via relaxing breathing.

In this connection, any one of Velcro, a webbing, a leather lock or a buckle may be further disposed on one portion of the head fixing means 220 to easily fix the movement of the head. The present disclosure is not limited thereto.

Next, the forehead fixing means 221 may be formed by connecting two points on the ring line of the head fixing means 220 to fix the forehead of the user.

The forehead fixing means 221 fixes the forehead of the user to restrict the movement of the cervical spine, which is advantageous for keeping the cervical spine in a C-shape.

In this connection, any one of Velcro, webbing, leather lock or buckle may be formed on one portion of the forehead fixing means 221 so that the forehead can be easily fixed.

The fixing strip 210 of the arm or shoulder fixing means 200 attaches to or winds around the strap support and fixes the user's arm or shoulder. Thus, the relaxation of muscles such as pectoralis major muscle, pectoralis minor muscle, rectus abdominis muscle, and trapezius muscle or latissimus dorsi muscle can be easily performed, which is advantageous for muscle stretching. Further, the blood vessel may be expanded and the blood may be supplied smoothly to the head. This may help recovery and correction during a short correction period. There is an advantage that a separate correction mechanism, which is used for spine correction such as a abdomen band, is unnecessary.

Embodiment 3

Figure 8:
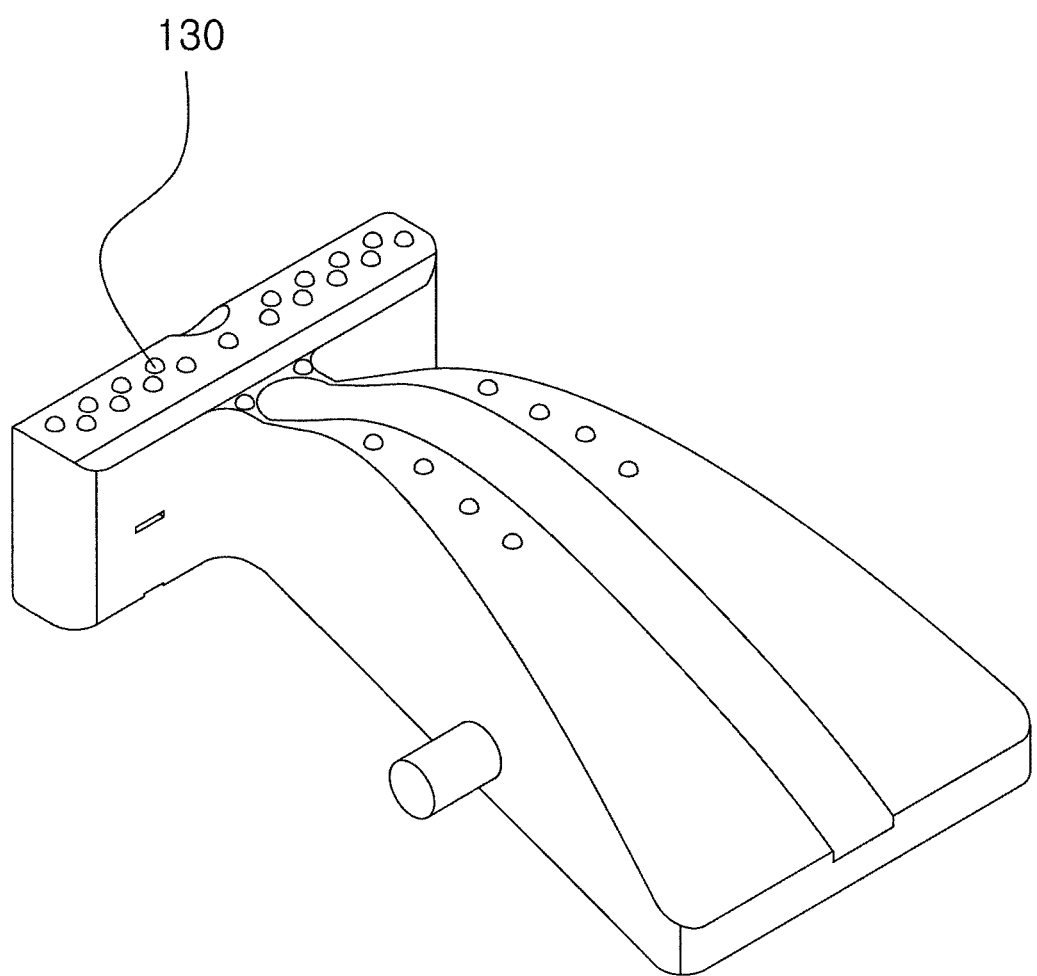
FIG. 8 is a perspective view of a cervicothoracic spine restorator according to an embodiment of the present disclosure.

In another example of the present disclosure, roughness structure 130 may optionally be included, as shown in FIG. 8.

The roughness structure 130 may protrude from a top face of the main body 100.

The roughness structure 130 may allow the stimulation to be applied to the muscles of the pectoralis major muscle, pectoralis minor muscle, rectus abdominis muscle, and trapezius muscle or latissimus dorsi muscle. There is an advantage that the relaxation of the muscles can be easily performed.

Embodiment 4

Figure 9:
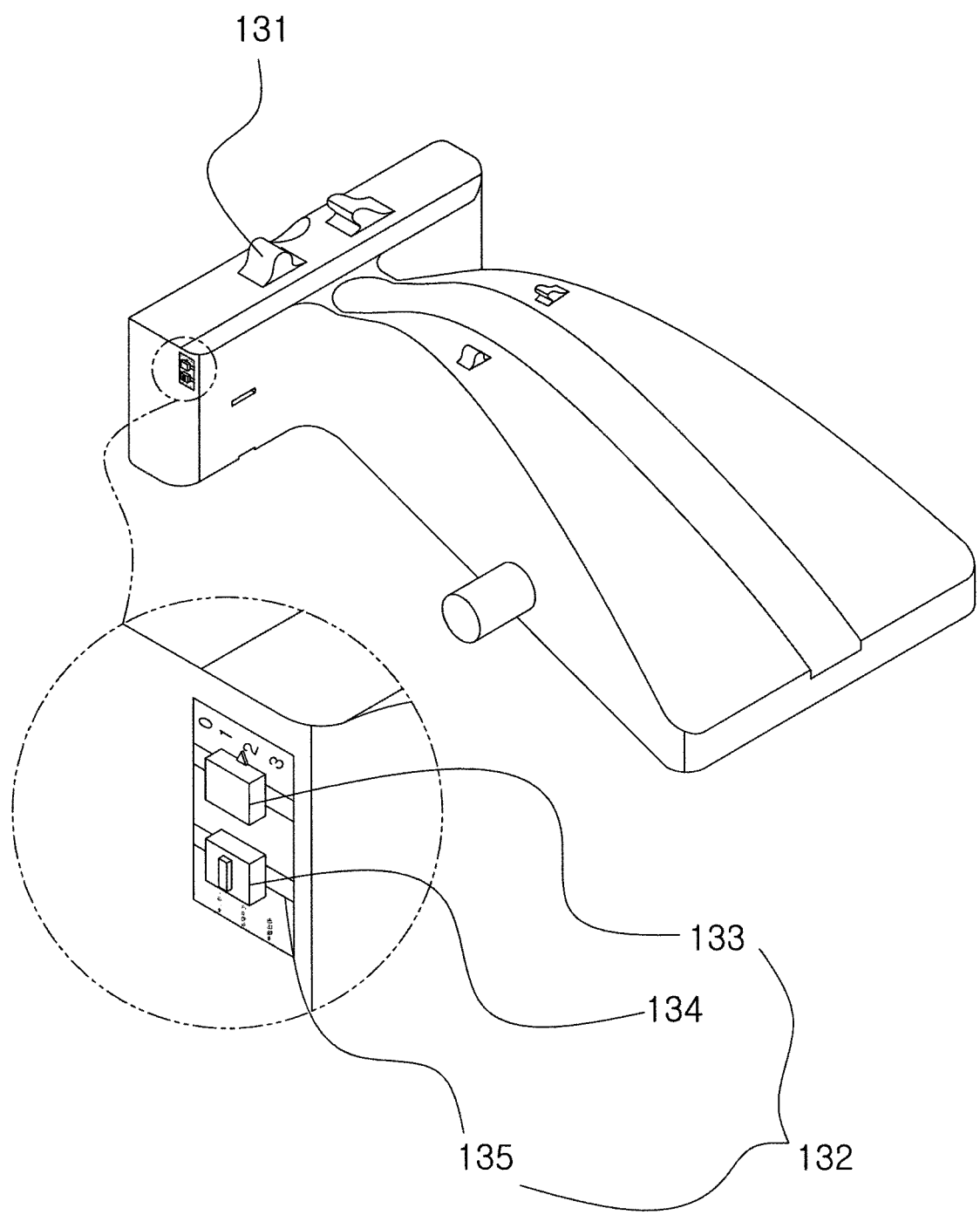
FIG. 9 is a perspective view of a cervicothoracic spine restorator according to an embodiment of the present disclosure.
Figure 10:
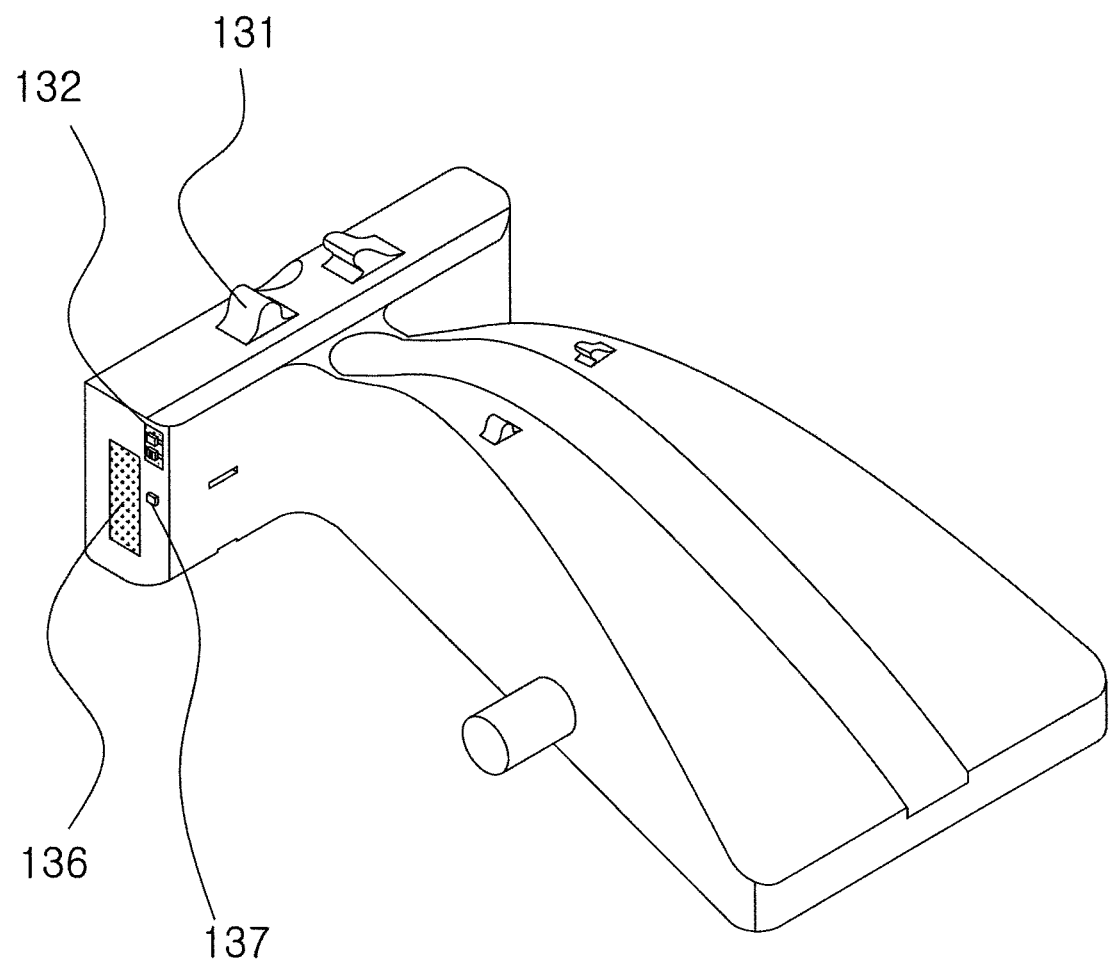
FIG. 10 is a perspective view of a cervicothoracic spine restorator according to an embodiment of the present disclosure.

As shown in FIGS. 9 and 10, spaded rotating protrusions 131 may be configured to be rotatable or vibrate based on an electrical signal of a control unit formed inside the main body 100.

The rotating protrusions 131 protrude outwardly from a top face of the main body 100. The rotating protrusions 131 may perform rotation and/or vibration based on an electrical signal. Thus, the muscles such as pectoralis major muscle, pectoralis minor muscle, rectus abdominis muscle, and trapezius muscle or latissimus dorsi muscle may be subjected to massage functions such as tapping, rubbing, and the like.

In addition, a control interface 132 may be further included to control the intensity and mode of the rotation or vibration of the rotating protrusions 131.

The control interface 132 may further include an intensity adjusting interface 133, a mode selection interface 134, and an interface movement guide 135.

In addition, the control interface 132 may protrude outwardly from the main body 100, and may be formed on the left or right side of the main body.

The control interface 132 may be formed so as to be protruded outward on the side surface so as to be easily manipulated in a state where the shoulder or arm is fixed by the fixing straps of the arm or shoulder fixing means 200.

The intensity adjustment interface 133 may be configured to adjust the intensity of the motion of the rotating protrusions 131.

The intensity adjustment interface 133 may be configured so that the rotating protrusions 131 can be rotated or vibrated to a desired intensity to easily perform the muscle relaxation.

In addition, the mode selection interface 134 may be configured to selection the mode of motion of the rotating protrusions 131.

The mode selection interface 134 may be configured to select the rotation or vibration of the rotating protrusions 131 so that the massage type suitable for a user's preference may be performed.

When the user selects the tapping mode, the body of the user may be messaged by the vibration of the rotating protrusions 131. When the user selects the press-rubbing mode, the rotating protrusions 131 may rotate so as to press-rub the user's body.

In addition, the mode selection interface 134 may be configured to select a combined massage function to perform a combination of the vibration and rotation of the rotating protrusions 131.

The interface movement guide 135 may be formed so that the intensity adjustment interface 133 or the mode selection interface 134 may be slidably guided and fixed.

The interface movement guide 135 may allow the position of the intensity adjustment interface 133 and the mode selection interface 134 to be adjusted in a direction in which the interface movement guide 135 extends. Thus, there is an advantage that massage can be appropriately performed at the intensity and mode suited to the user's taste.

Embodiment 5

As shown in FIG. 10, a speaker unit 136 for a radio or audio device, which is formed on one side of the main body 100, may be further included.

Preferably, the speaker unit 136 may be formed on one of the left and right sides of the main body 100 so that, upon listening to music or sound, the user's mind and body may be stabilized at the same time as the correction of the spine or cervical spine.

More preferably, the speaker unit 136 may be configured to allow the user to selectively listen to music according to a user's taste. To this end, the user may use a Bluetooth signal to control an audio device having the speaker unit 136

In this connection, a speaker unit controller 137 is further disposed apart from the speaker unit 136. The speaker unit controller 137 may be configured to allow the user to turn on or off the speaker unit 136 and turn on or off the Bluetooth signal at the same time.

The speaker unit 136 and the speaker unit controller 137 may be located at a position spaced apart from the control interface 132 such that the user manipulation may be easily performed via a simple operation of the user. However, the present invention is not limited thereto.

Embodiment 6

Figure 11:
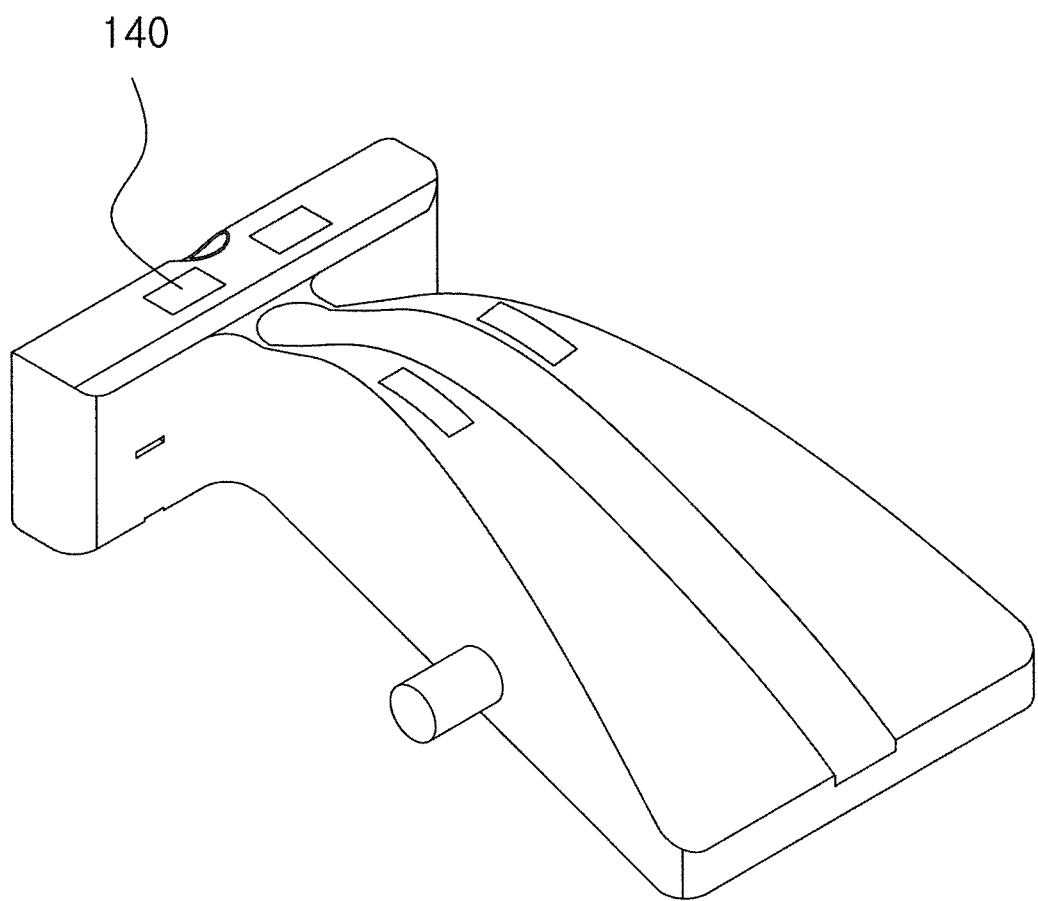
FIG. 11 is a perspective view of a cervicothoracic spine restorator according to an embodiment of the present disclosure.

As shown in FIG. 11, a pharmaceutical pad 140 may be stacked on a top face of the main body 100. The pad may further include one or more selected from various topical analgesics.

The pharmaceutical pad 140 may be formed to protrude outwards on a top face of the main body 100. Thus, at the same time as the correction of the user's cervical spine or spine, the topical analgesic contained in the pharmaceutical pad 140 may be absorbed into a to-be-treated portion of the body such as the back muscle. Thus, the muscle may be easily relaxed in a short time.

Preferably, the pharmaceutical pad 140 is formed on a top face of the main body 100. However, the present disclosure is not limited thereto.

The pharmaceutical pad 140 may include one or more selected from nonwoven fabric made of one or more of PE (polyethylene), PP (polypropylene) or PU (polyurethane) or a fabric made of one or more of polyester, cotton, spandex, nylon, liquid silicone, hydrogel or bio-cellulose.

In addition, the main body 100 may be easily adhered and fixed to the affected part of the user via adhesiveness of the pharmaceutical pad 140.

Embodiment 7

Figure 12:
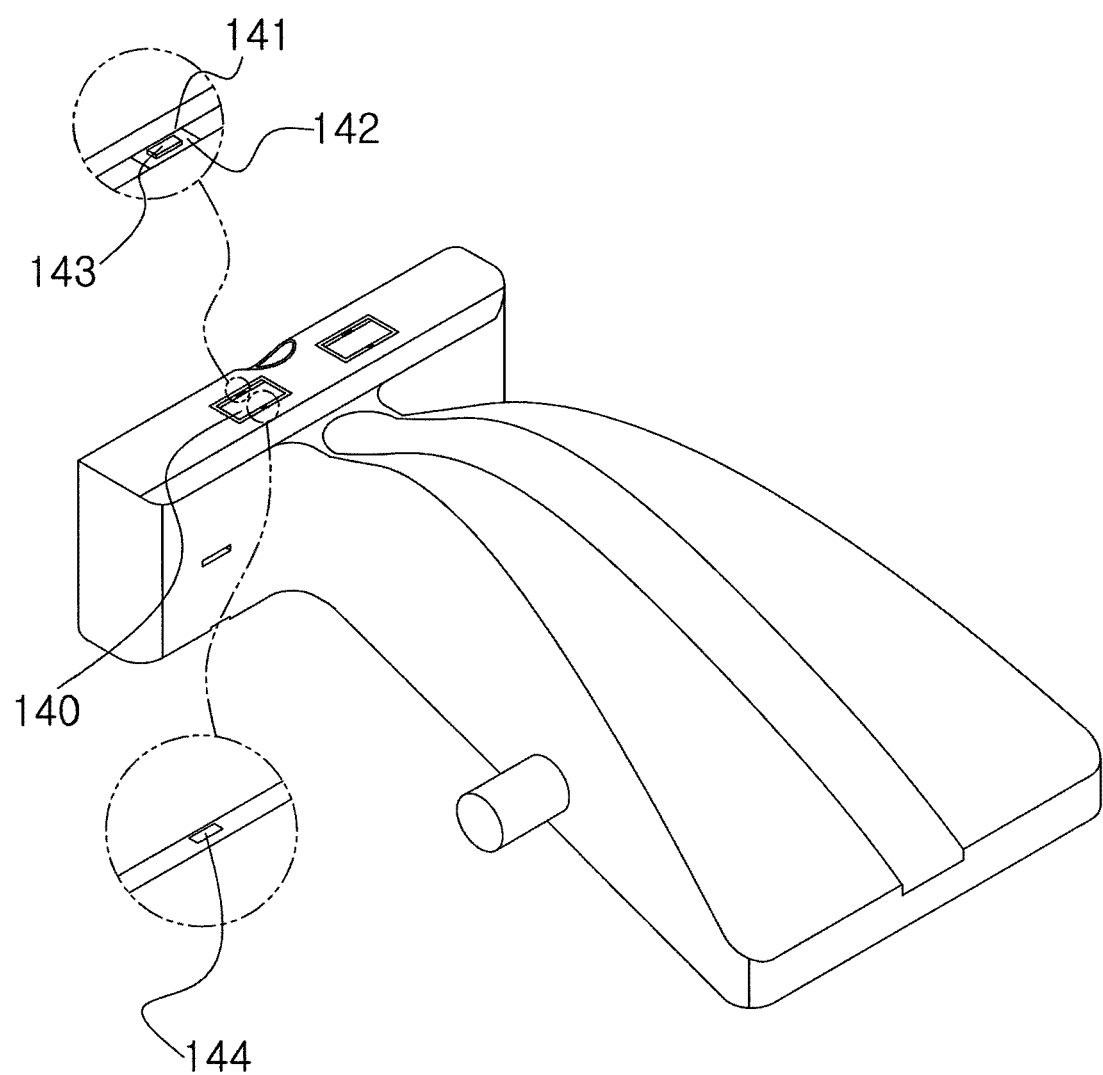
FIG. 12 is a perspective view of a cervicothoracic spine restorator according to an embodiment of the present disclosure.

As shown in FIG. 12, a housing 141, a housing cover 142, fixing portion 143, and housing locking means 144 may be optionally included to protect the pharmaceutical pad 140.

The housing 141 may be protruded outwardly to surround a rim of the pharmaceutical pad 140.

In this connection, the housing 141 may be inserted into the main body 100 by an external force, so that the medical pad 140 may be adhered to the affected part of the user.

The housing cover 142 may be formed in the inside of the housing 141 so as to cover an open portion of the housing 141.

The housing cover 142 may be slidably opened and closed by a user's operation.

When the housing 141 is opened by the housing cover 142, the housing cover 142 may be slidably inserted into the housing along the inner circumferential surface of the housing 141.

Accordingly, when the medical pad 140 is adhered to the main body with the housing 141 being inserted into the main body by the external force, the housing 141 may not be interfered by the housing cover 142.

The fixing portion 143 may protrude outwardly from a face of the housing cover 142.

When the housing 141 is opened, the user slides the housing cover 142 in the direction in which the housing 141 is opened by gripping the fixing portion 143. When the housing 141 is closed, the user slides the housing cover 142 in the direction in which the housing 141 is closed, by gripping the fixing portion 143.

The housing locking means 144 protrudes in a direction facing the housing cover 142 from a face of the housing 141. When the housing locking means 144 is engaged with the housing handle, the housing cover 142 may be fixed.

In this connection, the housing locking means 144 is formed in a through-hole shape so that the housing cover 142 can be easily fixed. Thus, the housing cover 142 protruding outwardly may be engaged with the housing locking means 144 by a simple operation.

Therefore, the pharmaceutical pad 140 may be protected by the housing cover 142 and the housing locking means 144, thereby facilitating the reuse of the pharmaceutical pad 140.

Embodiment 8

Figure 13:
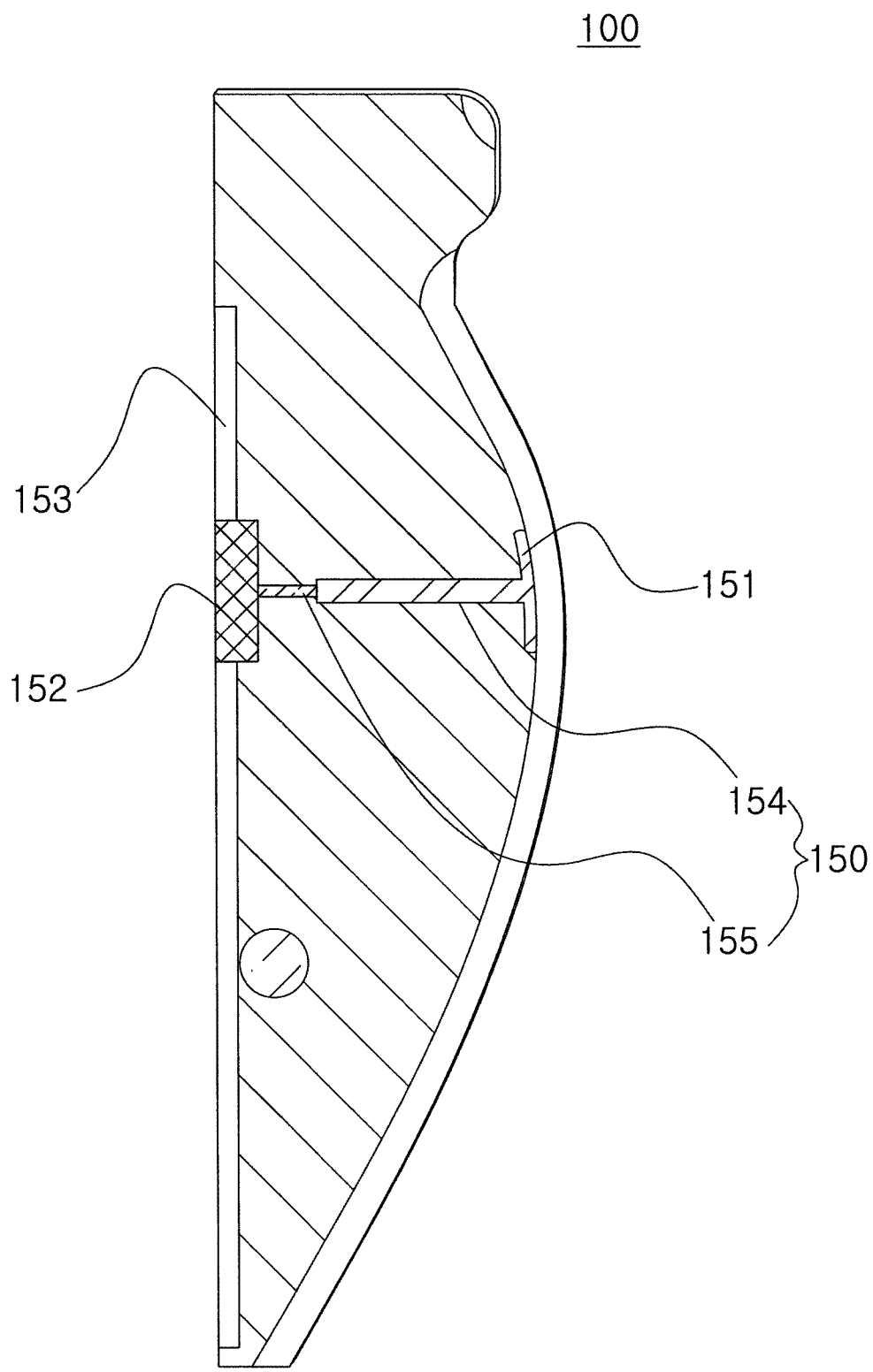
FIG. 13 is a cross-sectional view taken along a line A-A' of a cervicothoracic spine restorator according to in accordance with the embodiment of the present disclosure.

As shown in FIG. 13, a height adjustment unit 150, a height maintaining unit 151, a height adjustment unit support 152, and a slid portion 153 may be further included so that the height of the main body 100 can be easily adjusted.

The height adjustment unit 150, the height maintaining unit 151, the height adjustment unit support 152, and the slid portion 153 may be contained in the back support portion 120 to allow the height of the back support portion 120 to be adjusted according to the body skeleton size or preference of the user. However, the present disclosure may be not limited to the contained state in the back support portion 120.

The height adjustment unit 150 may be operated in an electric, hydraulic or pneumatic manner and may inserted into the main body 100. This unit 150 may be divided into a first height adjustment sub-unit 154 and a second height adjustment sub-unit 155.

The first height adjustment sub-unit 154 may be operatively associated with the height maintaining portion 151 to be described later, and may be movable upwards or downwards by the user's control.

Further, the second height adjustment sub-unit 155 may have a top portion inserted into the first height adjustment sub-unit 154 and may move so as to adjust the vertical position of the first height adjustment sub-unit 154.

Accordingly, the vertical position or level of the first height adjustment sub-unit 154 is adjusted by the operation of the second height adjustment sub-unit 155 according to the body skeleton size and the preference of the user, so that the correction of the user's spine or cervical spine can be easily performed.

The height maintaining portion 151 may be extended horizontally above the height adjustment unit 150.

The height maintaining portion 151 may be curved in a convex manner. Thus, the main body 100 may be maintained to be a curved manner to conform to the curved manner of the height maintaining portion 151.

The height maintaining portion 151 may prevent a secondary accident that may be caused by the operation of the height adjustment unit 150.

The height adjustment unit support 152 may be electrically, hydraulically or pneumatically operated and may be configured to adjust a vertical level of the height adjustment unit 150 while being disposed below the height adjustment unit 150.

The slid portion 153 may be configured such that the height adjustment unit support 152 is slidably moved on the bottom face of the main body 100.

When the user relaxes the lumbar spine in the spine region, the height adjustment unit support 152 may be slid along the slid portion 153 and then fixed at an appropriate position.

The second height adjustment sub-unit 155 may then be adjusted to adjust the level of the first height adjustment sub-unit 154 to a level desired by the user, thereby adjusting a vertical position of the first height adjustment sub-unit 154 based on the user's body skeleton size and choice.

In order to fix the height adjustment unit support 152, the height adjustment unit support 152 may move inwardly along the inner circumferential surface of the slid portion 153 and may be engaged with a stopper formed on the inner circumferential surface of the slid portion 153. The present invention is not limited thereto.

Further, the second height adjustment sub-unit 155 receives a device such as an electric, hydraulic or pneumatic mechanism, a spring or a screw to adjust the level of the first height adjustment sub-unit 154. Thus, the height adjustment unit 150 may be configured to easily adjust the height of the height adjustment unit 150 itself. However, the present invention is not limited thereto.

Embodiment 9

Figure 14:
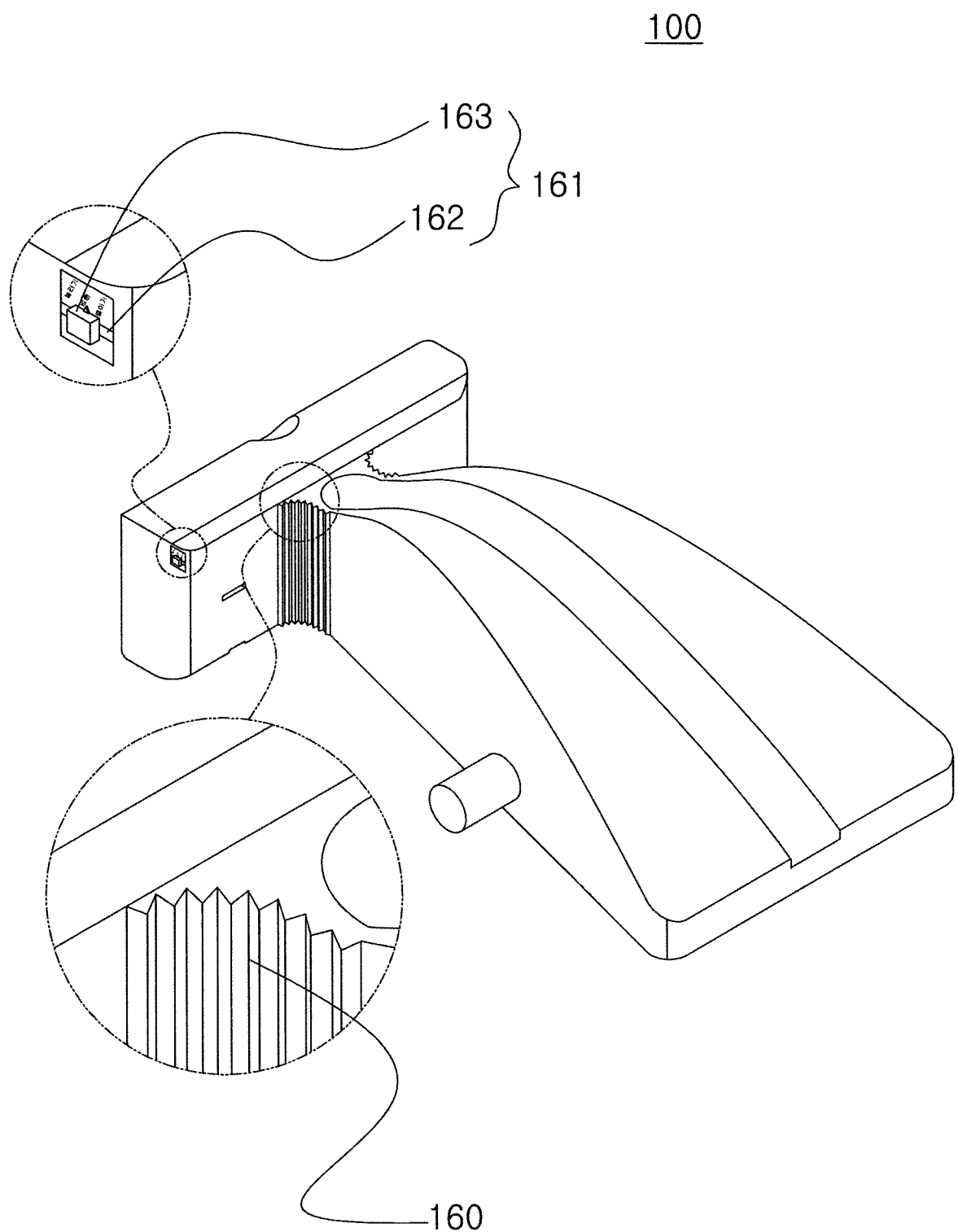
FIG. 14 is a perspective view of a cervicothoracic spine restorator according to an embodiment of the present disclosure.

As shown in FIG. 14, an expandable or shrinkable portion 160 may be further included so as to expand or shrink the main body 100.

The expandable or shrinkable portion 160 is formed at a joint position between the cervical spine support portion 110 and the back support portion 120. The expandable or shrinkable portion 160 may expand or shrink to advantageously reduce the pressure applied to the user's cervical spine and spine.

In this connection, the expandable or shrinkable portion 160 is easily stretched and contracted. To this end, an air pump or a motor may be further included in the main body 100 so that the expandable or shrinkable portion 160 may be extended or contracted by the air pump or the motor.

Accordingly, the expandable or shrinkable portion 160 may be formed in a wrinkled shape to easily expand or shrink.

Therefore, when the extension of the main body 100 is required by the air pump or the motor, the expandable or shrinkable portion 160 formed in a wrinkled shape may be stretched. When the shrinkage of the main body 100 is required, the expandable or shrinkable portion 160 contracts. Thus, it is easy to adjust the length of the main body 100 to a size suitable for the user's body condition. Further, the expandable or shrinkable portion 160 may be expanded or shrink while the user being fixed to the main body 100, so that the pressure imposed to the body can be reduced by relaxing the cervical spine or spine of the user.

An expand or shrink control interface unit 161 may also be formed. The interface unit 161 includes an interface movement guide 162 and an expand or shrink control interface 163 for easy expansion or shrink of the expandable or shrinkable portion 160.

The expanding or shrinkable control interface unit 161 may be formed on the left or right side face of the main body 100 so that the expandable or shrinkable portion 160 can be extended or reduced by a simple operation.

In this connection, the user may select one of the expanding mode, a stopping mode, or a shrinkage mode by sliding the expansion or shrink control interface 163 along the interface movement guide 162. Then, the expandable or shrinkable portion 160 may be expanded or shrink by turning on or off the motor or pump connected to the expandable or shrinkable portion 160.

The interface movement guide 162 may slidably guide the expand or shrink control interface 163. Thus, the expandable or shrinkable portion 160 may be enabled or disabled by operating the motor or pump connected to the expandable or shrinkable portion 160.

A size of the expandable or shrinkable portion 160 may be adjusted by a simple operation by further including the expanding or shrink adjusting control interface 163.

Optionally, the expandable or shrinkable portion 160 may be configured such that the cervical spine support portion 110 and the back support portion 120 may be separated from each other. Thus, separating and engaging the cervical spine support portion 110 and the back support portion 120 of the main body 100 may allow extending or contracting the main body 100 to a length corresponding to the user's body condition. The present invention is not limited thereto.

INDUSTRIAL APPLICABILITY

The present disclosure provides a cervicothoracic spine restorator in which a fixing structure is further included, such that relaxation of muscles can be easily performed and recovery and correction can be achieved in a short correction time.

What is claimed is:

1. A cervicothoracic spine restorator comprising:
a main body having a curved outer top face configured to contact a cervical spine and a spine in a fixed manner;
fixing means including a fixing strap outwardly extending from a right or left side face of the main body and protruding outwardly to surround a lower side face of the main body;
a pharmaceutical pad disposed on a top face of the main body so as to protrude outwardly therefrom, wherein the pharmaceutical pad contains a topical analgesic;
a housing protruding outwardly to surround an edge of the pharmaceutical pad;
a housing cover formed inside the housing so as to cover an outer face of the housing;
a housing fixing portion protruding outwardly from one face of the housing cover; and
a housing locking portion protruding in a direction facing the housing cover from a face of the housing, wherein the housing fixing portion is engaged with the housing locking portion to fix the housing cover.

2. The cervicothoracic spine restorator of claim 1, wherein the main body includes:
a cervical spine support portion protruding upwardly to support a cervical spine to be kept in a C-shape, wherein a head support groove is defined in the cervical spine support portion; and
a back support portion extending downwardly from the cervical spine support portion and protruding outwardly, wherein the back support portion includes a spine support portion to support a spine to be kept in a C-shape and to be fixed in a correct position.

3. The cervicothoracic spine restorator of claim 2, wherein the back support portion includes a recess inwardly defined in a right or left lateral edge thereof to facilitate contraction of a back muscle.

4. The cervicothoracic spine restorator of claim 2, further comprising:
head fixing means spaced from a top of the cervical spine support portion to surround a head and fix the head; and
forehead fixing means protruding outwardly from one side of the head fixing means to fix a forehead.

5. The cervicothoracic spine restorator of claim 1, further comprising at least one roughness structure protruding outwardly from a top of the main body.

6. The cervicothoracic spine restorator of claim 1, further comprising a rotating protrusion protruding outwardly from a top face of the main body, wherein the rotating protrusion is configured to vibrate or rotate based on an electrical signal from a controller disposed inside the main body.

7. The cervicothoracic spine restorator of claim 1, further comprising:
a height adjustment unit contained in the main body;
a height maintaining portion extending horizontally from a top of the height adjustment unit;
a height adjustment unit support disposed below the height adjustment unit, wherein the height adjustment unit support is configured to adjust a vertical position of the height adjustment unit; and
a slid portion configured to allow the height adjustment unit support to slidably move on a bottom face of the main body along the slid portion.

8. The cervicothoracic spine restorator of claim 1, further comprising an expandable or shrinkable portion disposed on the main body to expand or shrink the main body or to divide the main body into two portions.

9. A cervicothoracic spine restorator comprising:
a main body having a curved outer top face configured to contact a cervical spine and a spine in a fixed manner;
fixing means including a fixing strap outwardly extending from a right or left side face of the main body and protruding outwardly to surround a lower side face of the main body;
a height adjustment unit contained in the main body;
a height maintaining portion extending horizontally from a top of the height adjustment unit;
a height adjustment unit support disposed below the height adjustment unit, wherein the height adjustment unit support is configured to adjust a vertical position of the height adjustment unit; and
a slid portion configured to allow the height adjustment unit support to slidably move on a bottom face of the main body along the slid portion.

10. The cervicothoracic spine restorator of claim 9, wherein the main body includes:
a cervical spine support portion protruding upwardly to support a cervical spine to be kept in a C-shape, wherein a head support groove is defined in the cervical spine support portion; and
a back support portion extending downwardly from the cervical spine support portion and protruding outwardly, wherein the back support portion includes a spine support portion to support a spine to be kept in a C-shape and to be fixed in a correct position.

11. The cervicothoracic spine restorator of claim 10, wherein the back support portion includes a recess inwardly defined in a right or left lateral edge thereof to facilitate contraction of a back muscle.

12. The cervicothoracic spine restorator of claim 10, further comprising:

head fixing means spaced from a top of the cervical spine support portion to surround a head and fix the head; and forehead fixing means protruding outwardly from one side of the head fixing means to fix a forehead.

13. The cervicothoracic spine restorator of claim 9, further comprising at least one roughness structure protruding outwardly from a top of the main body.

14. The cervicothoracic spine restorator of claim 9, further comprising a rotating protrusion protruding outwardly from a top face of the main body, wherein the rotating protrusion is configured to vibrate or rotate based on an electrical signal from a controller disposed inside the main body.

15. The cervicothoracic spine restorator of claim 9, further comprising a pharmaceutical pad disposed on a top face of the main body so as to protrude outwardly therefrom, wherein the pharmaceutical pad contains a topical analgesic.

16. The cervicothoracic spine restorator of claim 9, further comprising an expandable or shrinkable portion disposed on the main body to expand or shrink the main body or to divide the main body into two portions.

* * * * *